United States Patent
Inoue

(10) Patent No.: US 9,232,888 B2
(45) Date of Patent: Jan. 12, 2016

(54) OPTICAL TOMOGRAPHIC IMAGING APPARATUS, IMAGE PROCESSING APPARATUS, AND OPTICAL TOMOGRAPHIC IMAGE DISPLAY METHOD

(71) Applicant: CANON KABUSHIKI KAISHA, Tokyo (JP)

(72) Inventor: Hiroyuki Inoue, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 13/967,568

(22) Filed: Aug. 15, 2013

(65) Prior Publication Data

US 2014/0063449 A1 Mar. 6, 2014

(30) Foreign Application Priority Data

Aug. 30, 2012 (JP) ................. 2012-189802

(51) Int. Cl.
| | |
|---|---|
| *A61B 3/00* | (2006.01) |
| *A61B 3/10* | (2006.01) |
| *G06T 11/00* | (2006.01) |
| *G06F 19/00* | (2011.01) |

(52) U.S. Cl.
CPC ............. *A61B 3/0058* (2013.01); *A61B 3/0041* (2013.01); *A61B 3/102* (2013.01); *G06F 19/321* (2013.01); *G06F 19/3406* (2013.01); *G06T 11/001* (2013.01)

(58) Field of Classification Search
CPC ... A61B 3/0041; A61B 3/0058; G06T 11/003
USPC ......................................................... 351/206
See application file for complete search history.

(56) References Cited

U.S. PATENT DOCUMENTS

| | | | | |
|---|---|---|---|---|
| 7,793,217 | B1* | 9/2010 | Kim et al. | 715/255 |
| 8,214,766 | B1* | 7/2012 | Berger et al. | 715/838 |
| 2007/0242069 | A1* | 10/2007 | Matsue et al. | 345/428 |
| 2008/0100612 | A1* | 5/2008 | Dastmalchi et al. | 345/418 |
| 2011/0110576 | A1* | 5/2011 | Kreeger et al. | 382/132 |
| 2011/0228110 | A1* | 9/2011 | Thorson | 348/207.11 |
| 2012/0249961 | A1* | 10/2012 | Muto | 351/208 |

FOREIGN PATENT DOCUMENTS

| | | |
|---|---|---|
| JP | 2006-092201 A | 4/2006 |
| JP | 2012-045225 A | 3/2012 |

* cited by examiner

*Primary Examiner* — Jordan Schwartz
(74) *Attorney, Agent, or Firm* — Carter, DeLuca, Farrell & Schmidt, LLP

(57) ABSTRACT

Provided is an optical tomographic imaging apparatus including: a tomographic image acquiring unit for acquiring a tomographic image of an eye of a patient; a scanning type two-dimensional image acquiring unit for acquiring a two-dimensional image of the eye; a patient information storage unit for storing images acquired by the tomographic image acquiring unit and the scanning type two-dimensional image acquiring unit together with patient information; and a display unit. The display unit performs a list display of patient information of at least one patient stored in the patient information storage unit. When one patient is selected from a patient group in the list display, at least one past acquired tomographic image and a two-dimensional image acquired substantially simultaneously with the tomographic image of the patient are displayed as thumbnail images in a list. An image parameter of the tomographic image displayed as the thumbnail image is changeable.

15 Claims, 12 Drawing Sheets

FIG. 1A

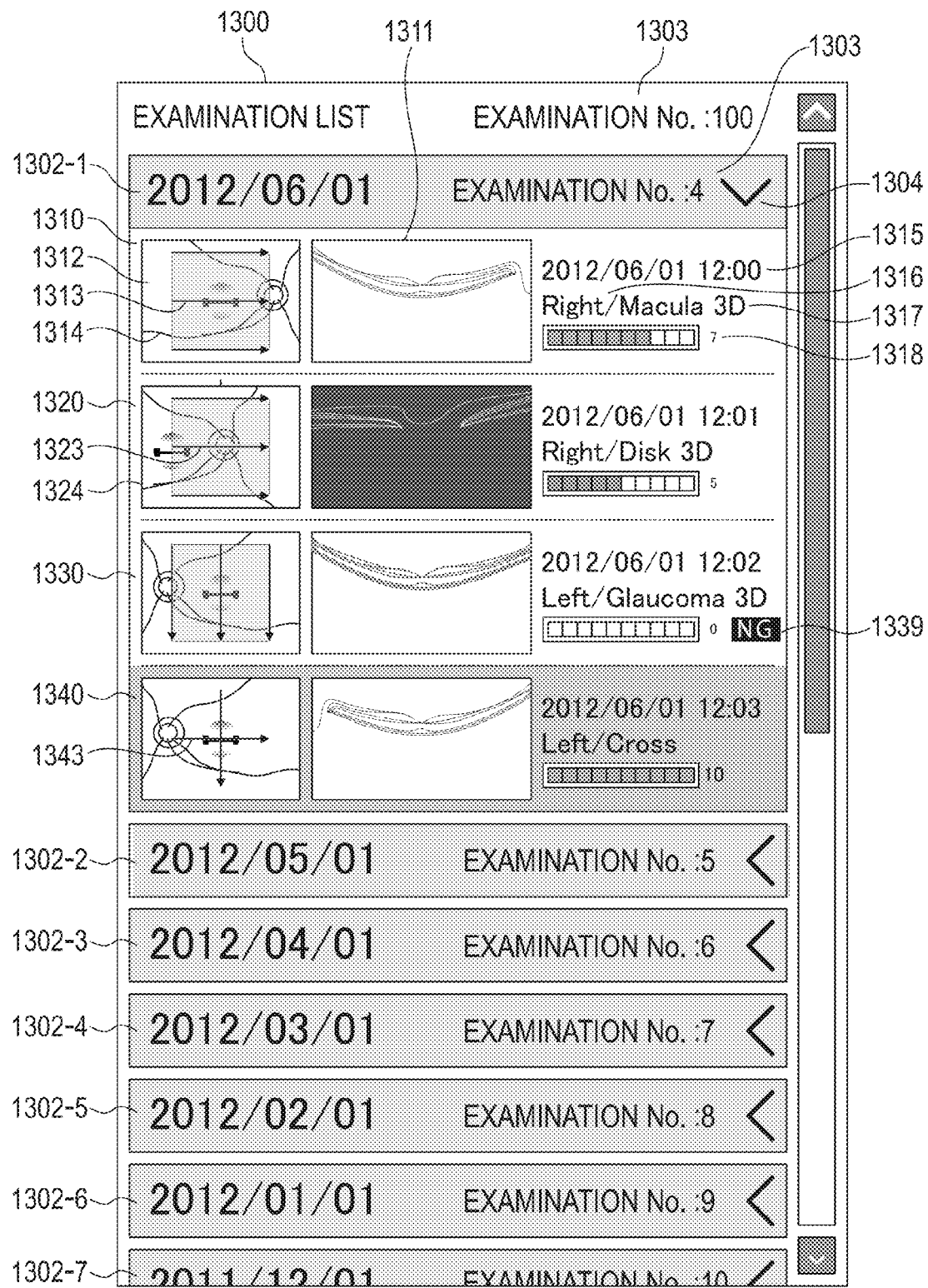

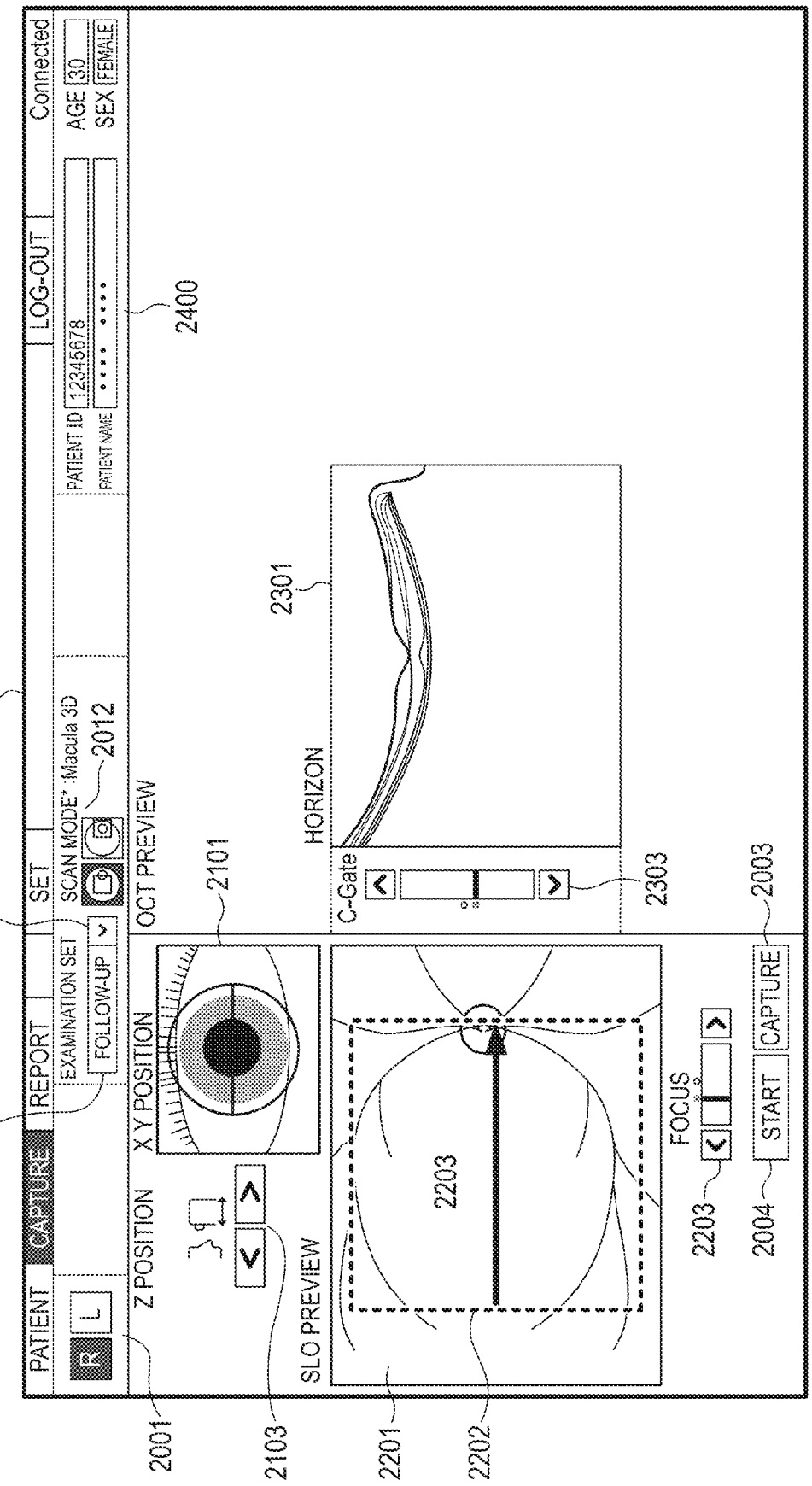

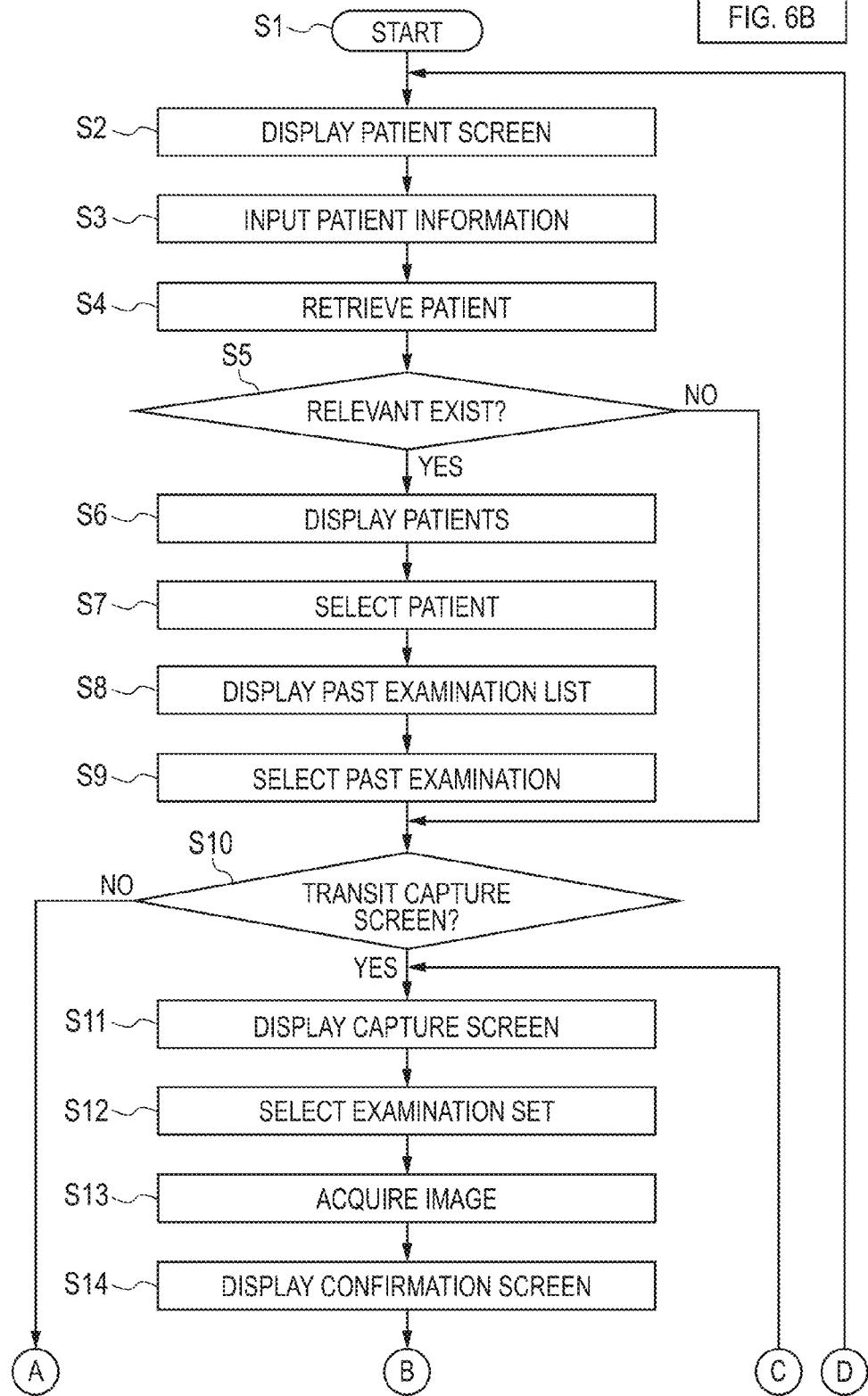

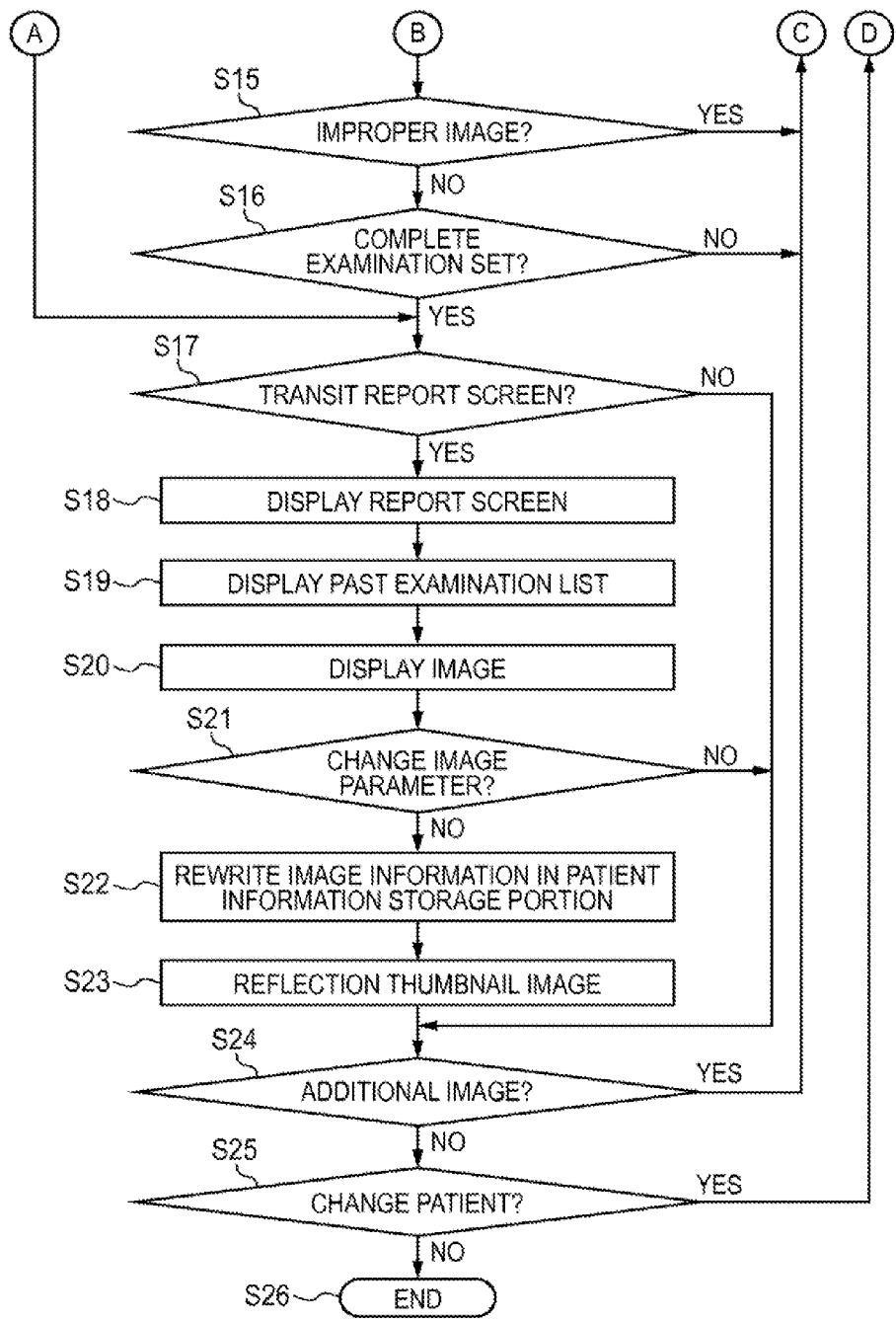

OPTICAL TOMOGRAPHIC IMAGING APPARATUS, IMAGE PROCESSING APPARATUS, AND OPTICAL TOMOGRAPHIC IMAGE DISPLAY METHOD

BACKGROUND OF THE INVENTION

1. Field of the Invention

The present invention relates to an optical tomographic imaging apparatus, an image processing apparatus, and an optical tomographic image display method.

2. Description of the Related Art

Currently, there are various types of ophthalmological instruments using an optical instrument. For instance, as an optical instrument for observing an eye, there are used various instruments such as an anterior ocular segment imaging instrument, a fundus camera, and a confocal laser scanning ophthalmoscope (scanning laser ophthalmoscope: SLO). In particular, an optical tomographic imaging apparatus, which performs optical coherence tomography (OCT) utilizing an interference phenomenon of multi-wavelength light, is an apparatus capable of obtaining a tomographic image of a sample with high resolution. For this reason, the optical tomographic imaging apparatus is becoming an indispensable apparatus as an ophthalmological instrument for a specialist of retina in the outpatient field. In addition, the optical tomographic imaging apparatus is used not only for ophthalmologic use but also for an endoscope or the like. This apparatus is hereinafter referred to as "OCT apparatus". The OCT apparatus is widely used for acquiring a tomographic image of a retina of a fundus of an eye to be inspected or a tomographic image of an anterior ocular segment such as a cornea in ophthalmologic diagnosis or the like.

The OCT apparatus is capable of spliting measuring light having low coherence into reference light and measuring light, and irradiating an object to be inspected with the measuring light to cause return light from the object to be inspected to interfere with the reference light, to thereby measure a layer of the object to be inspected. Further, the OCT apparatus can obtain a tomographic image with high resolution by scanning the sample with the measuring light. Further, the OCT apparatus one-dimensionally scans a specific area with the measuring light so as to acquire a two-dimensional tomographic image. Further, the one-dimensional scan for acquiring the two-dimensional tomographic image is repeated while shifting the position, to thereby acquire a three-dimensional image.

Here, in the ophthalmologic diagnosis, an operator may refer to data of images photographed in the past for detailed diagnosis of a lesion of the eye to be inspected or its variation with time. In addition, the operator may refer to photography data in the past and reads the photography condition for performing the photography in the same composition and the same condition (follow-up photography) in order to study variation with time of individual lesions. Therefore, it is desired to display the data of images photographed in the past in a display form such that the data can be easily looked up.

In contrast, Japanese Patent Application Laid-Open No. 2006-092201 discloses a three-dimensional image processing apparatus for medical images, in which multiple pieces of three-dimensional data are listed as thumbnail images that are processed by rendering for two-dimensional image projection. In addition, Japanese Patent Application Laid-Open No. 2012-045225 discloses an image processing apparatus for ophthalmologic use, which selects one tomographic image from three-dimensional data and displays the selected image as a thumbnail image. The thumbnail image as used herein means a low resolution image in which the number of horizontal and vertical pixels is reduced so that its pattern can be seen at a glance.

However, it may be easier for the operator to grasp a feature and to retrieve desired data if an image parameter of the thumbnail image in the display is adjusted to be an optimal value for the operator.

SUMMARY OF THE INVENTION

In view of the above-mentioned problem, it is an object of the present invention to provide an optical tomographic imaging apparatus and an optical tomographic image display method, in which desired inspection data can be easily retrieved so that improvement of examination efficiency can be expected.

According to one embodiment of the present invention, there is provided an optical tomographic imaging apparatus including: a tomographic image acquiring unit for acquiring a tomographic image by scanning an object to be inspected with measuring light; a two-dimensional image acquiring unit for acquiring a two-dimensional image of the object to be inspected; a patient information storage unit for storing images acquired by the tomographic image acquiring unit and the two-dimensional image acquiring unit together with patient information; a display unit; a display control unit for instructing the display unit about an image to be displayed; and a display input unit for accepting an external input to the display control unit via the image displayed on the display unit. The display control unit includes an image parameter changing unit for changing an image parameter of the image, and is configured to control the display unit to perform a list display of patients whose patient information is stored in the patient information storage unit and to perform a list display of thumbnail images of the patient information of the selected patient. The display input unit is configured to accept a selection of one patient from the list display of patients and a change of the image parameter. The image parameter changing unit is configured to change the image parameter of at least one of the thumbnail images in accordance with an instruction to change the image parameter accepted by the display input unit. The display control unit is configured to control the display unit to display an image after the image parameter is changed.

Further, according to one embodiment of the present invention, there is provided an image processing apparatus including: an image acquiring unit for acquiring an image of an object to be inspected; an image generation unit for generating a thumbnail image based on the image acquired by the image acquiring unit; and an image processing unit for allowing image processing performed on the image acquired by the image acquiring unit to be reflected on the thumbnail image.

Further, in order to achieve the above-mentioned object, according to one embodiment of the present invention, there is provided an optical tomographic image display method for displaying an image acquired by an optical tomographic Imaging apparatus, the optical tomographic imaging apparatus including: a tomographic image acquiring unit for acquiring a tomographic image scanning an object to be inspected with measuring light; a two-dimensional image acquiring unit for acquiring a two-dimensional image of the object no be inspected; a patient information storage unit for storing images acquired by the tomographic image acquiring unit and the two-dimensional image acquiring unit together with patient information; and a display unit, the display method including: performing, by the display unit, a list display of patients whose patient information is stored in the patient information storage unit; selecting one patient from the list display of patients via a screen displayed on the display unit; performing, by the display unit, a list display of thumbnail images of the patient information of the selected patient; changing an image parameter of at least one of the thumbnail images in accordance with an image parameter change in a display of the acquired image, the image parameter change being instructed on the display screen; and controlling the display unit to display an image after the image parameter is changed.

According to the present invention, the optical tomographic imaging apparatus in which desired inspection data can be easily retrieved so that improvement of examination efficiency can be expected can be provided. That is, it is possible to provide a thumbnail image whose feature is easy for the operator to grasp.

Further features of the present invention will become apparent from the following description of exemplary embodiments with reference to the attached drawings.

BRIEF DESCRIPTION OF THE DRAWINGS

FIG. 1A is an example of an explanatory diagram of a patient screen of an optical tomographic imaging apparatus according to the present invention, and FIG. 1B is an example of an explanatory diagram of a past examination list in the patient screen.

FIGS. 3A, 3B, and 3C are examples of an explanatory diagram of individual steps of a patient search process in the patient screen of the optical tomographic imaging apparatus according to the present invention.

FIG. 4A is an example of an explanatory diagram of a capture screen for displaying a real time image (moving image) before photography by the optical tomographic imaging apparatus according to the present invention.

FIG. 5A is an example of an explanatory diagram of a report screen for displaying a detailed tomographic image of the optical tomographic imaging apparatus according to the present invention, and FIG. 5B is an example of an explanatory diagram in a case where a mode order tab is selected in the past examination list of the report screen.

FIG. 6 is comprised FIGS. 6A and 6B showing an example of an explanatory diagram of an operation flow according to the present invention.

DESCRIPTION OF THE EMBODIMENTS (Main Body Structure)

Figure 2A:
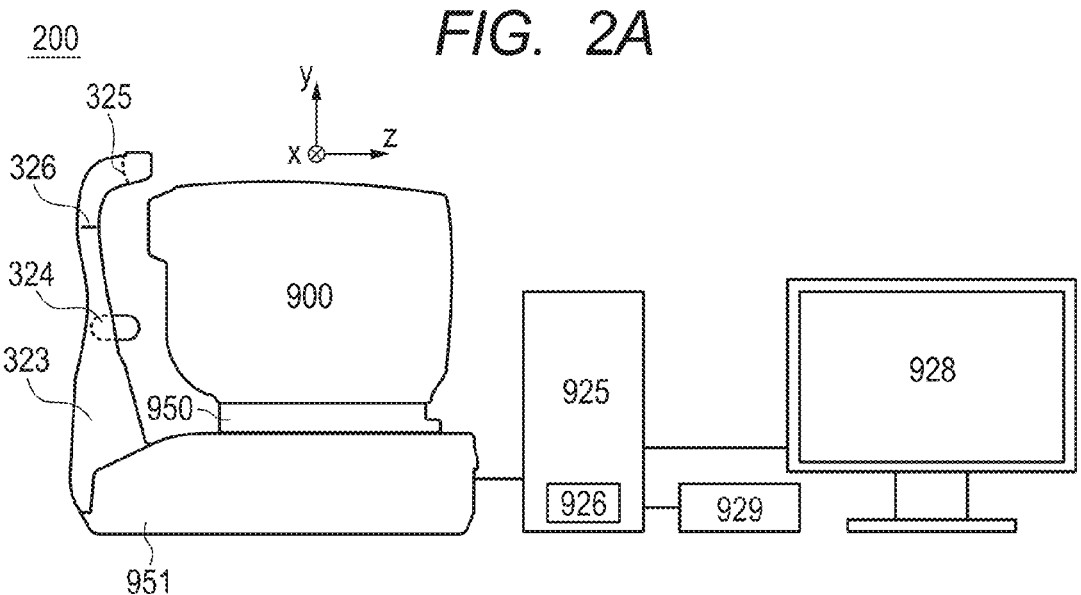
FIG. 2A is a diagram illustrating an example of an outline of the optical tomographic imaging apparatus according to the present invention.

FIG. 2A is a side view of an optical tomographic imaging apparatus according to an embodiment of the present invention. An optical tomographic imaging apparatus 200 includes an acquiring portion (measuring optical system) 900 for acquiring an anterior ocular segment image, and a two-dimensional image and a tomographic image of an eye to be inspected, and a stage portion 950 as a moving portion capable of moving the image acquiring portion 900 in X, Y, and Z directions using a motor (not shown). The optical tomographic imaging apparatus 200 also includes a base portion 951 in which a spectroscope described later is disposed.

As described later in detail, the image acquiring portion 900 scans an object to be inspected with light for acquiring an image of the object to be inspected, so as to photograph the object no be inspected no acquire an image of the object to be inspected.

A personal computer 925 serves also as a control portion for the stage portion, and performs control of the stage portion, control of an alignment operation, construction of the tomographic image as described later, and the like. A hard disk 926 is a storage portion for storing a program for tomographic photography and serves also as a patient information storage portion for storing patient information and various photography data.

A monitor 928 serves as a display portion, and an input portion 929 gives an instruction to the personal computer. Specifically, the input portion 929 includes a keyboard and a mouse. In other words, the monitor 928 is a single common monitor for displaying a patient screen, a capture screen before photography, a confirmation screen after photography, and a report screen in a time division manner, which are described later. The monitor 928 is disposed not on the image acquiring portion 900 side but on the personal computer 925 side.

A face support 323 includes a chin rest 324 capable of being moved up and down by a motor (not shown), a forehead rest 325, and an eye height line 326 disposed at a center of a movement range in the height direction of an objective lens described later. The face of a subject is fixed by placing the chin of the subject on the chin rest 324 and pushing the forehead to the forehead rest 325 so that a height of the eye of the subject may be substantially the same as a height of the eye height line 326. Thus, the eye to be inspected is roughly positioned at the acquiring portion 900.

(Structure of Measuring Optical System and Spectroscope)

Figure 2B:
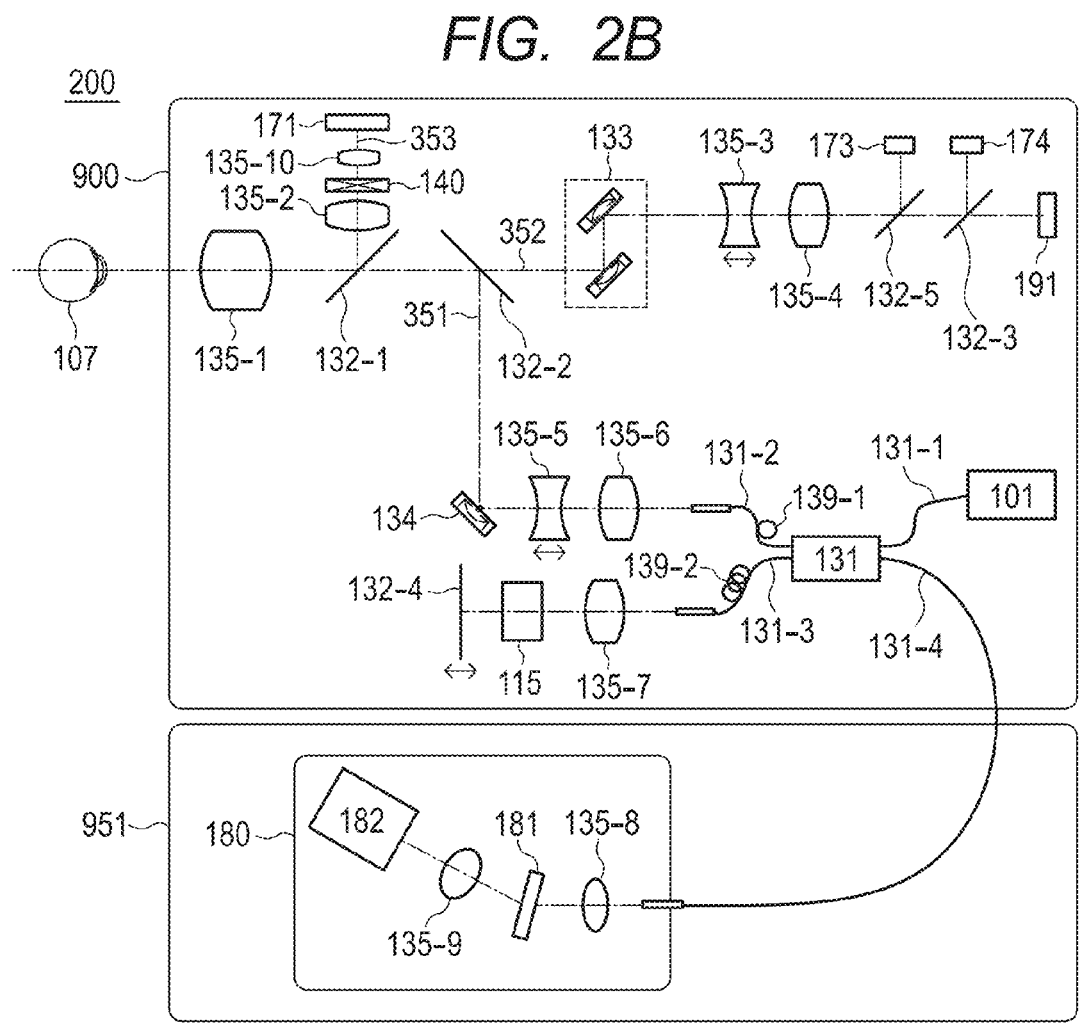
FIG. 2B is an example of an explanatory diagram of a measuring optical system as an image acquiring portion of the optical tomographic imaging apparatus according to the present invention.

A structure of the measuring optical system and the spectroscope according to this embodiment is described with reference to FIG. 2B. First, the inside of the acquiring portion 900 is described. An objective lens 135-1 is disposed to be opposed to an eye to be inspected 107, and a first dichroic mirror 132-1 and a second dichroic mirror 132-2 are disposed on an optical axis of the objective lens 135-1. Those dichroic mirrors split an optical path into an optical path 351 for an OCT optical system, an optical path 352 for a fixation target and an SLO optical system for observation of the eye to be inspected and acquisition of a two-dimensional image thereof, and an optical path 353 for anterior ocular segment observation, in accordance with the wavelength band. The SLO optical system corresponds to a two-dimensional image acquiring unit for acquiring a two-dimensional image of the eye to be inspected in the present invention. In addition, measuring light used in the optical system corresponds to measuring light for the two-dimensional image.

The optical path 352 for the SLO optical system and the fixation target includes an SLO scanning unit 133, lenses 135-3 and 135-4, a mirror 132-5, a third dichroic mirror 132-3, a photodiode 173, an SLO light source 174, and a fixation target 191. The mirror 132-5 is a perforated mirror or a prism on which a hollow mirror is formed by vapor deposition, so as to separate illumination light of the SLO light source 174 from return light from the eye to be inspected. The third dichroic mirror 132-3 separates an optical path of the SLO light source 174 from an optical path to the fixation target 191 in accordance with the wavelength band. The SLO scanning unit 133 deflects the light beams emitted from the SLO light source 174 and the fixation target 191 to scan the eye to be inspected 107. The SLO scanning unit 133 includes an X scanner for scanning in an X direction and a Y scanner for scanning in a Y direction. In this embodiment, the X scanner is formed of a polygon mirror for high speed scanning, and the Y scanner is formed of a galvano mirror. The lens 135-3 is driven by a motor (not shown) for the SLO optical system and for focusing on the fixation target. The SLO light source 174 emits light having a wavelength of approximately 780 nm. The photodiode 173 detects return light from the eye to be inspected. The fixation target 191 emits visible light so as to urge the subject to stare.

The light emitted from the SLO light source 174 is reflected by the third dichroic mirror 132-3, passes through the mirror 132-5, the lenses 135-4 and 135-3, and is deflected by the SLO scanning unit 133 to scan the eye to be inspected 107. In other words, in the present invention, it is preferred that the two-dimensional image acquiring unit be a scanning type two-dimensional image acquiring unit, but it is possible to use other type of two-dimensional image acquiring unit depending on the apparatus structure. The return light from the eye to be inspected 107 propagates backward along the same path as the projection light, and is reflected by the mirror 132-5 so as to be guided to the photodiode 173. The light of the fixation target 191 passes through the third dichroic mirror 132-3 and the mirror 132-5, and lenses 135-4 and 135-3, and is deflected by the SLO scanning unit 133 so as to scan the eye to be inspected 107. In this case, the fixation target 191 is blinked in accordance with a movement of the SLO scanning unit so as to form an arbitrary shape at an arbitrary position on the eye to be inspected 107, and hence the subject is urged to stare.

In the optical path 353 for anterior ocular segment observation, there are disposed lenses 135-2 and 135-10, a split prism 140, and an anterior ocular segment observation CCD 171 for detecting infrared light. This CCD 171 is sensitive to a wavelength of illumination light for anterior ocular segment observation (not shown), specifically a wavelength of approximately 970 nm. The split prism 140 is disposed at a position conjugate with a pupil of the eye to be inspected 107, and it is possible to detect a distance of the acquiring portion 900 in the Z direction (front and back direction) with respect to the eye to be inspected 107 as a split image of the anterior ocular segment.

As described above, the optical path 351 of the OCT optical system constitutes the OCT optical system and is used for photographing a tomographic image of the eye to be inspected 107. More specifically, the optical path 351 is used for acquiring an interference signal for forming a tomographic image. An XY scanner 134 is used for scanning the eye to be inspected with light. The XY scanner 134 is illustrated as a single mirror but is formed of galvano mirrors for scanning in two directions of X and Y axes.

Lenses 135-5 and 135-6 are disposed. The lens 135-5 is driven by a motor (not shown) in order to focus light from an OCT light source 101 emitted from a fiber 131-2 connected to an optical coupler 131 on the eye to be inspected 107. By this focusing, the return light from the eye to be inspected 107 simultaneously forms a spot image at an end of the fiber 131-2 and enter the fiber 131-2.

Next, configurations of an optical path from the OCT light source 101, a reference optical system, and the spectrometer are described. The configurations include the OCT light source 101, a reference mirror 132-4, a dispersion compensation glass 115, the optical coupler 131, optical fibers 131-1 to 131-4 in a single mode connected to the optical coupler 131 to be integrated, a lens 135-7, and a spectrometer 180.

The above-mentioned components constitute a Michelson interferometer. The light emitted from the OCT light source 101 is split into measuring light on the optical fiber 131-2 side and reference light on the optical fiber 131-3 side through the optical fiber 131-1 via the optical coupler 131.

The measuring light illuminates the fundus of the eye to be inspected 107 to be observed through the optical path of the OCT optical system described above and reaches the optical coupler 131 through the same optical path due to reflection and scattering by the eye to be inspected.

The optical coupler 131 combines the measuring light with the reference light to form interference light. In this case, interference occurs when an optical path length of the measuring light and an optical path length of the reference light become substantially equal to each other. The reference mirror 132-4 is held so as to be adjusted in an optical axis direction by a motor and a drive mechanism (not shown) and is capable of adjusting the optical path length of the reference light to that of the measuring light varying depending on the eye to be inspected 107. The interference light is guided to the spectrometer 180 through the optical fiber 131-4.

Further, a polarization adjusting portion 139-1 is provided for the measuring light in the optical fiber 131-2. A polarization adjusting portion 139-2 is provided for the reference light in the optical fiber 131-3. Those polarization adjusting portions each have a part in which the optical fiber is looped several times. This looped part is rotated about the longitudinal direction of the fiber to twist the fiber. In this manner, the polarization state of each of the measuring light and she reference light can be adjusted and matched to each other.

The spectrometer 180 includes lenses 135-8 and 135-9, a diffraction grating 181, and a line sensor 182. The interference light emitted from the optical fiber 131-4 is collimated through the lens 135-8 and dispersed by the diffraction grating 181 to form an image on the line sensor 182 by the lens 135-9.

The OCT optical system described above corresponds to a tomographic image acquiring unit of the present invention, which scans the eye to be inspected with measuring light so as to acquire a tomographic image.

Next, the periphery of the OCT light source 101 is described. The OCT light source 101 is a super luminescent diode (SLD) that is a typical low coherent light source. Light emitted from the light source 101 has a central wavelength of 855 nm and a wavelength band width of about 100 nm. In this case, the band width influences a resolution in an optical axis direction of a tomographic image to be acquired, and hence, is an important parameter.

Although the SLD is selected, the type of the OCT light source 101 is not particularly limited as long as the light source is capable of emitting low coherent light, and amplified spontaneous emission (ASE) or the like may also be used. Considering the measurement of an eye, near-infrared light is suitable for the central wavelength. Further, it is desired that the central wavelength be a shortest possible wavelength because the central wavelength influences a resolution in a lateral direction of a tomographic image to be acquired. For both the reasons, the central wavelength is set to 855 nm.

Although the Michelson interferometer is used as an interferometer in this embodiment, a Mach-Zehnder interferometer may be used. It is desired that the Mach-Zehnder interferometer be used in the case where an optical amount difference between the measuring light and the reference light is large, and the Michelson interferometer be used in the case where the optical amount difference is relatively small.

With the structure described above, a tomographic image of the eye to be inspected can be acquired, and it is possible to acquire a two-dimensional image of the eye to be inspected having high contrast even with near-infrared light. In addition, the acquired tomographic image and two-dimensional image are stored in the above-mentioned patient information storage unit together with information of the patient whose image has been acquired.

(Photography Method of Tomographic Image)

A photography method of a tomographic image using the optical tomographic imaging apparatus 200 is described. The optical tomographic imaging apparatus 200 can photograph a tomographic image of a predetermined section of she eye to be inspected 107 by controlling the XY scanner 134. First, the measuring light is deflected for scanning in the X direction as illustrated in she diagram, and a predetermined photographing number of information from a photography range of the eye to be inspected in the X direction are photographed by the line sensor 182. A brightness distribution on the line sensor 182 obtained at a certain position in the X direction is processed by Fast Fourier Transform (FFT), and the linear brightness distribution obtained by the FFT is converted into density information to be displayed on the monitor 928. This is referred to as "A-scan image".

In addition, a two-dimensional image in which multiple A-scan images are arranged is referred to as "B-scan image". After photographing multiple A-scan images for constructing one B-scan image, the scanning position in the Y direction is shifted and the scanning in the X direction is performed again so as to acquire multiple B-scan images.

The multiple B-scan images, or a three-dimensional image constructed of multiple B-scan images is displayed on the monitor 928 as described below, and hence can be used by the operator for diagnosis of the eye to be inspected.

(Structure of Patient Screen for Patient Search)

Figure 1A:
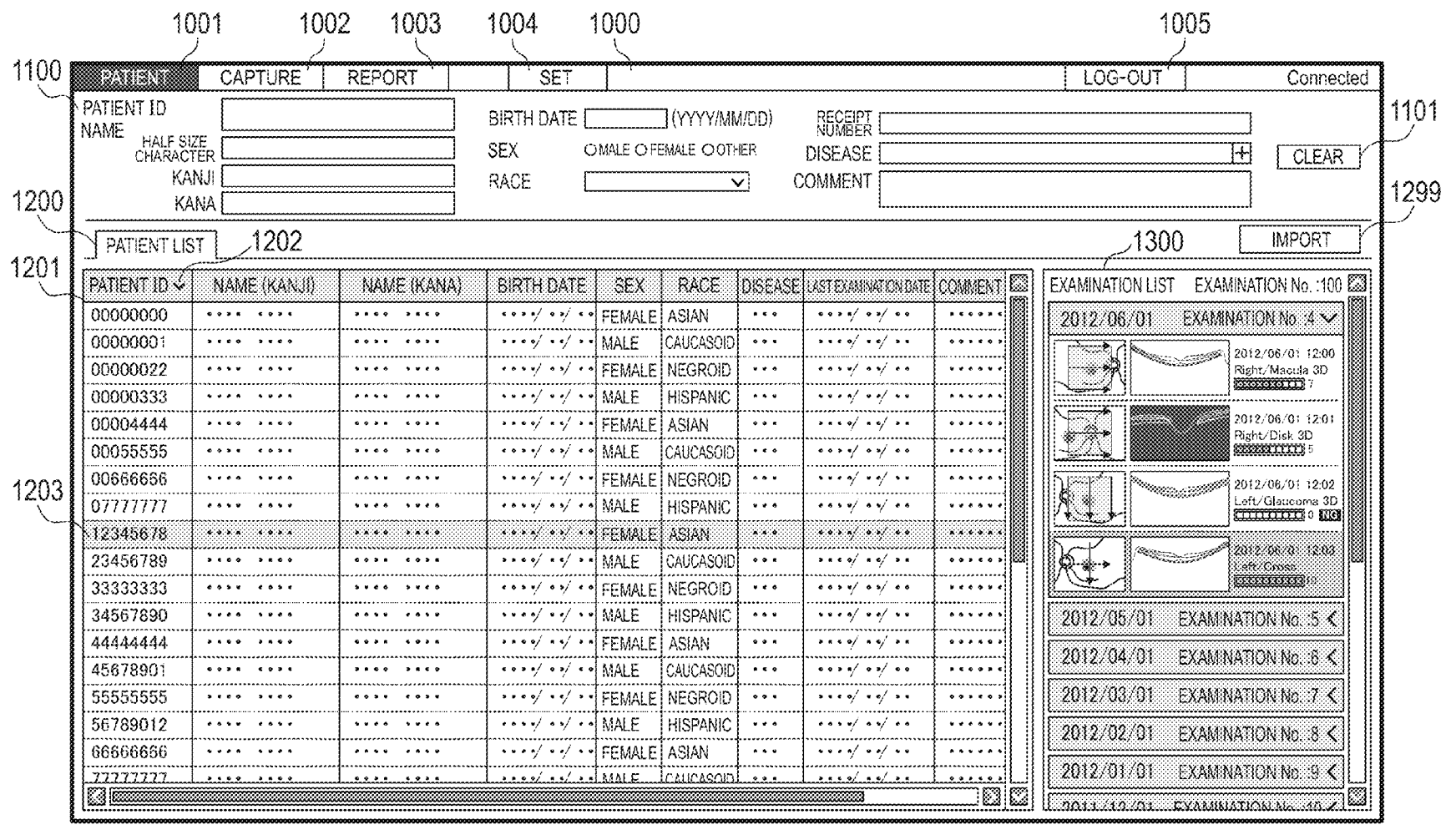

The patient screen according to this embodiment is described with reference to FIG. 1A. A patient screen 1000 is a screen for inputting and selecting patient information, which is displayed on the monitor 928 when the personal computer 925 executes an examination program before starting the examination. Buttons 1001, 1002, and 1003 are used for switching among the patient screen, a capture screen, and a report screen that are described later. A button 1004 is used for switching to a setting screen for various settings of a photography condition and the examination program. A log out button 1005 is used for finishing this software when the examination is finished. A patient information input portion 1100 is used for inputting patient information. In the case of a new patient, that is, in the case of a patient whose information is not stored in the patient information storage portion, the patient information is input so as to be stored in the patient information storage portion. In contrast, in the case of a patient whose information is already registered in the patient information storage portion, a search condition is input for searching for the patient from a patient list 1200 described later. Contents that can be input are a patient ID, a patient name, a date of birth, a sex, a race, a receipt number, a name of disease, a comment, and the like. A clear button 1101 is used for erasing all the information input in the patient information input portion 1100. The patient list 1200 is a part of listing patients stored in the patient information storage portion. In addition, if an item concerning the patient information is input to the patient information input portion 1100, the patient list 1200 displays only the patient corresponding to the input item. An import button 1299 is used for capturing external patient information into the patient information storage portion. An examination list 1300 is described later, in which past examination information of a patient selected in the patient list 1200 is displayed together with thumbnail images of photographed images.

(Structure of Patient List)

Here, a structure of the patient list 1200 is described in detail. The patient list 1200 includes a patient ID, a patient name, a date of birth, a sex, a race, a name of disease, the last examination date, and a comment of each patient stored in the examination information storage portion. A header 1201 of each item is displayed on an upper part of each item. Here, items to be displayed can be selected in a manner that only specific items are displayed among the above-mentioned items, and it is also possible to change an arrangement order and a column width of the item. In addition, by clicking the header portion corresponding to each item by a mouse or the like, it is possible to change an order of the patients of the patient list with reference to an ascending order or a descending order of the selected item. In this case, an arrow 1202 is displayed in the header portion of the item serving as a reference for sorting. Thus, it is possible to change a display of the patient list to be a display chat is easy for the operator to see.

In this patient list, the operator searches for a patient to be examined and selects the patient. Then, the selected patient is displayed in highlight as illustrated by 1203. If past inspection data of the selected patient is stored in the patient information storage portion, the examination information is displayed in the examination list 1300 described later. In addition, by operating a change button (not shown) (for example, in a pulldown menu that becomes available by right click of the mouse) in a state where a specific patient is selected, it is possible to edit the patient information that is already input.

Figure 3A:
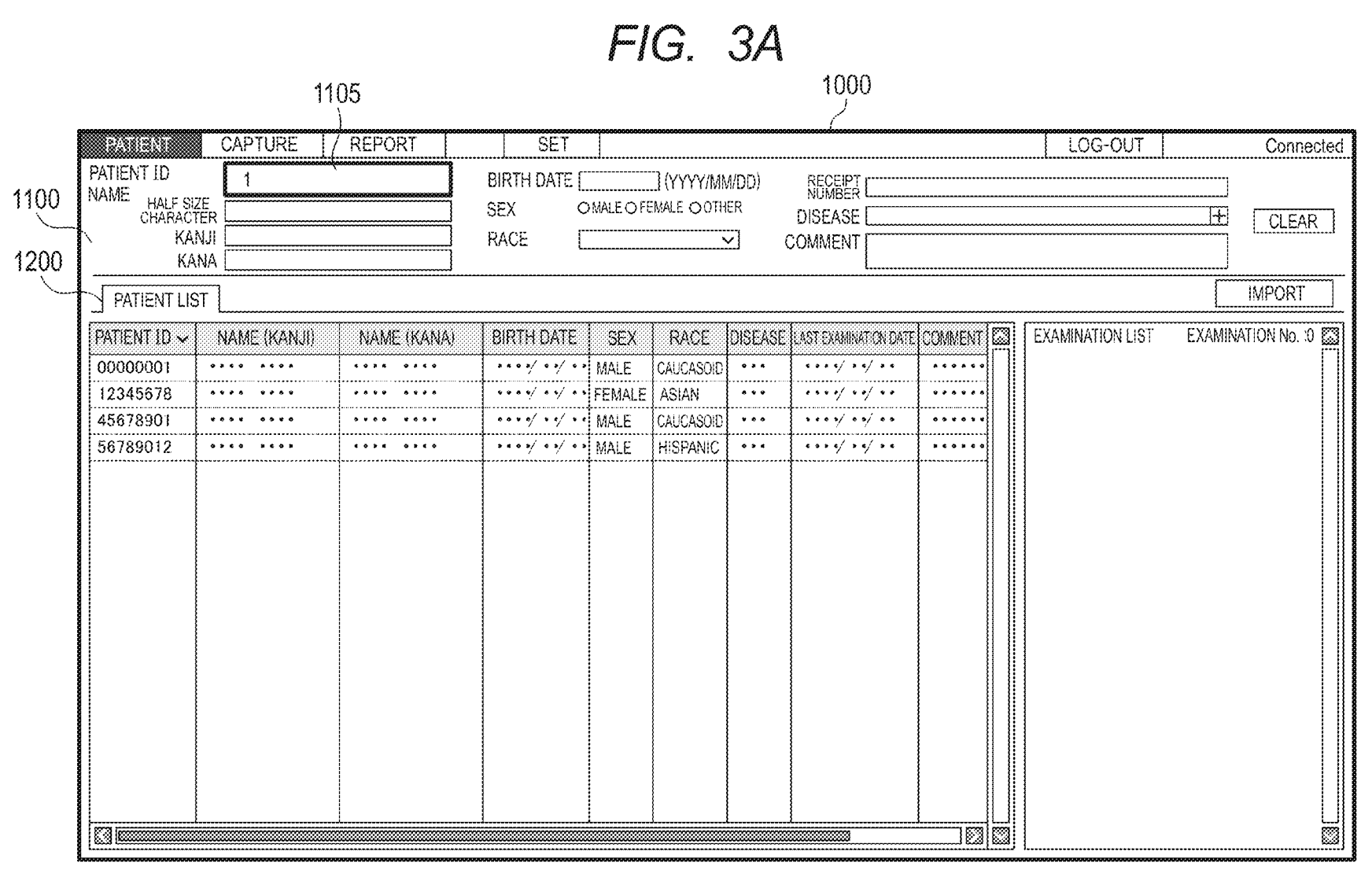
Figure 3B:
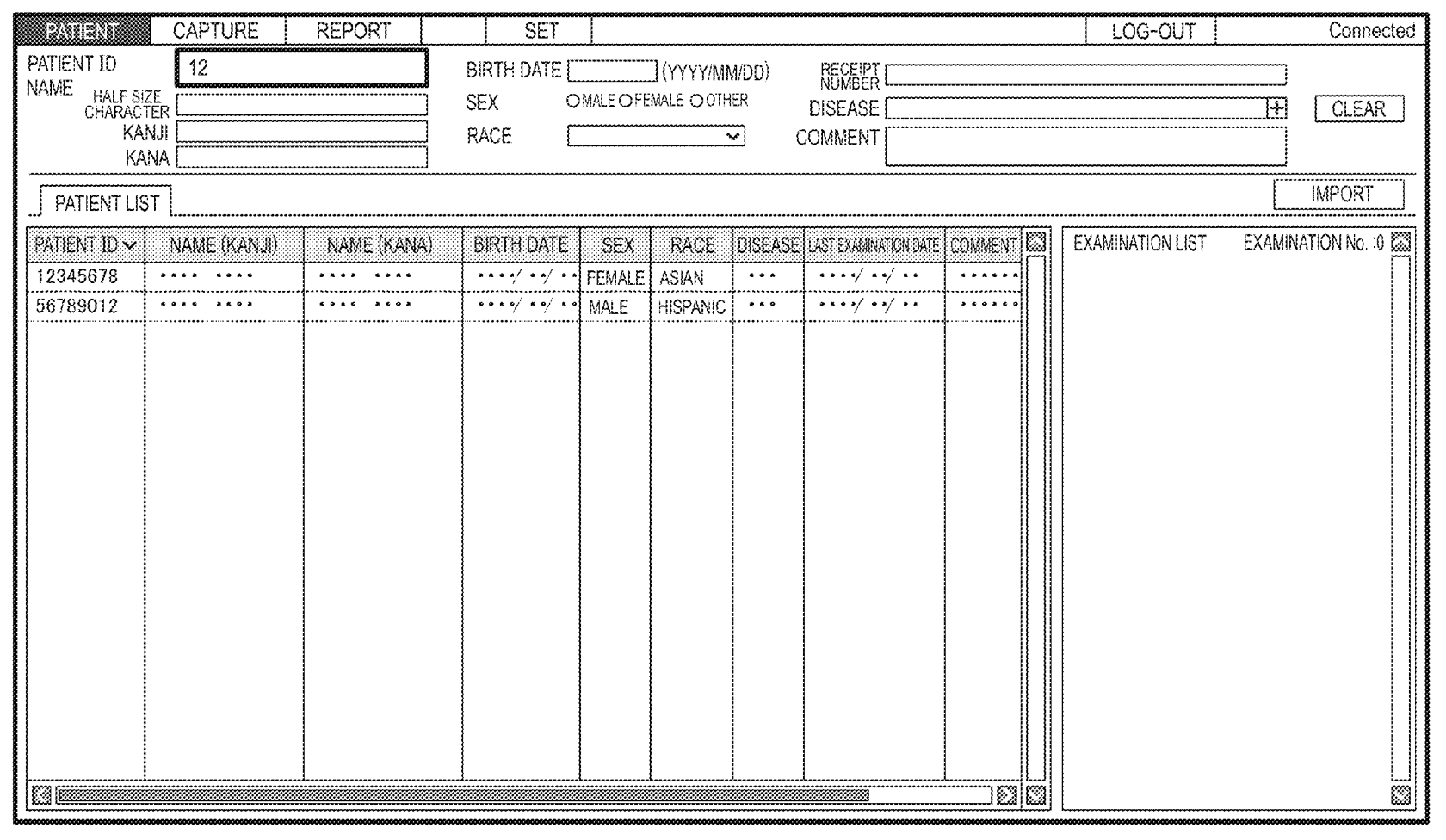
Figure 3C:
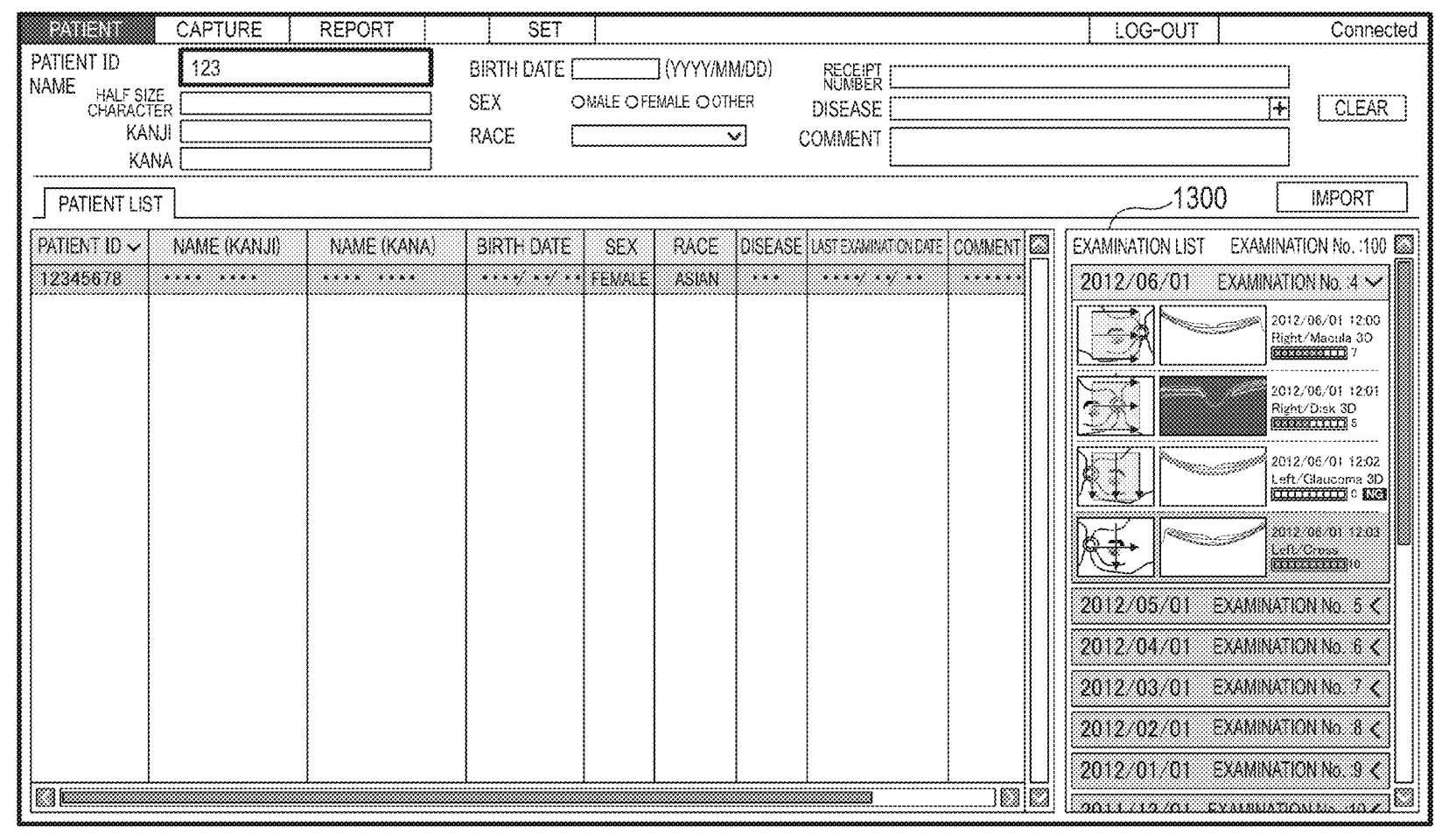

Here, when searching for a patient, it is also possible to input each information of the patient to be searched for in the patient information input portion 1100. Further, it is possible to narrow down the desired patient efficiently in shorter time by adopting an incremental search in which patients matching to input information are narrowed down from the examination list every time a character is input for the patient information. This example is illustrated in FIGS. 3A to 3C. Here, a process for searching for a patient having a patient ID "12345678" is illustrated. First, when "1" is input in the patient ID input portion 1105 of the patient information input portion 1100 as illustrated in FIG. 3A, the patient list 1200 is narrowed down to patients having the patient ID including "1". Next, when "2" is input following to "1", the patient list 1200 is narrowed down to patients having the patient ID including "12" as illustrated in FIG. 3B. Further, when "3" is input following to "2", the patient list 1200 is narrowed down to patients having the patient ID including "123" as illustrated in FIG. 3C. Here, FIG. 3C illustrates that patients narrowed down by the patient ID "123" from the patient list include only the desired patient (having a patient ID "12345678"). In other words, every time the patient information is input, a patient corresponding to the input patient information is retrieved from the patient information storage unit and is displayed on the monitor 928. In this way, by performing the incremental search, even if input of all pieces of information of a desired patient is not completed, it is possible to narrow down only by partial information. Therefore, the desired patient may be identified faster. In addition, the patient list 1200 is updated by always referring to the input information. Therefore, if patient information is input by mistake, the operator may recognize the input mistake earlier in the input process.

Further, when candidates are narrowed down to one patient, the patient may be automatically selected as illustrated in FIG. 3C, and past examination information of the patient may be displayed in the examination list 1300. In this way, it is also possible to grasp whether or not the retrieved patient is the desired patient in an intuitive manner on the basis of images photographed in the past.

Here, the example of search based on the patient ID is described above, but this is not a limitation. It is possible to search on the basis of other patient information, for example, a patient name, a date of birth, a sex, a race, a name of disease, or a comment. In addition, it is possible to search on the basis of multiple items. Also in this case, the narrow down process is the same as described above.

(Structure of Examination List)

Next, a characteristic structure of the examination list of the present invention is described with reference to FIG. 1B. In the examination list 1300, a list of past examinations of the selected patient is displayed. A number 1301 is a total number of pieces of past inspection data of the selected patient. Tabs 1302-1 to 1302-6 are inspection data group tabs in which pieces of photography data are grouped by date. The tab displays the date of photography, the number of pieces of inspection data 1303 on the date, and an expansion indicator 1304 indicating an expanded/collapsed state. Here, the inspection data group grouped by date is displayed in a descending order, that is, so that later date is displayed in an upper position. In addition, just after the patient is selected, only a tab for the latest date is expanded and the inspection data of the date is displayed as illustrated in FIG. 1B, while tabs for other date are collapsed so that the inspection data is not displayed. When each tab portion is operated (clicked by the mouse or the like), the inspection data group of the date of the collapsed tab is expanded and displayed.

Each inspection data displayed as one inspection data per photography as in inspection data A as 1310, inspection data B as 1320, inspection data C as 1330, and inspection data D as 1340. The individual pieces of inspection data grouped by the same date are sorted and displayed in an ascending order of time, that is, so that earlier time is displayed in an upper position. In addition, just after the patient is selected, the latest inspection data is automatically selected. In this case, the inspection data D (1340) is selected and is displayed in highlight. In a list display of thumbnail images of tomographic images, it is possible to sort by assigning a first priority to one of orders including a photography date and time order, a scanning pattern order, and a left/right eye order, and assigning a second priority to a remaining one of the orders. The pieces of inspection data are displayed in the ascending order of time in the example described above, but without limiting to this, it is possible to display the pieces of inspection data in the descending order of time.

Here, display contents of one inspection data are described in detail. For instance, the inspection data A (1310) is constituted of a thumbnail image 1311 of a typical tomographic image, a thumbnail image 1312 of a two-dimensional image (SLO image) of the eye to be inspected, photography date and time 1315, left/right information 1316 of the photographed eye, a scanning pattern name 1317, and a QI value 1318. In addition, if a determination whether the image is improper as described later is made by the operator, "NG" is displayed as illustrated by 1339 in the inspection data D (1330).

As to the tomographic thumbnail image 1311, in the case of photography for acquiring a single tomographic image, the tomographic image is displayed as the thumbnail image. In contrast, if multiple tomographic images are acquired, a tomographic image of a center position displayed as the thumbnail image, for example. In addition, if the eye to be inspected is scanned in a horizontal direction and in a vertical direction, an image acquired by the horizontal scan is displayed with priority, for example.

The SLO thumbnail image 1312 is an image acquired substantially simultaneously with acquiring the tomographic image, in which a scanning pattern 1313 for acquiring the tomographic image is overlapped on the SLO image. Here, the scanning pattern is a locus of light for acquiring the tomographic image by scanning the eye to be inspected. Examples thereof are a cross scan of scanning like a cross shape with one point as the center, and a 3D scan of scanning so as to fill the entire area to acquire a three-dimensional tomographic image as a result. In addition, the 3D scan includes a vertical 3D scan and a horizontal 3D scan depending on whether the priority is given in the vertical direction or in the horizontal direction. For instance, a 3D scan 1313 indicates a horizontal 3D scan of a predetermined area with a macular as the center, in which lines of the upper end, the lower end, and the center portion in the area scanned actually for acquiring the tomographic image, and the scan directions are indicated by arrows. In addition, when the 3D scan is performed, a projection image 1314 is displayed instead of the SLO image only in the scanned area as the SLO thumbnail image 1312 of the inspection data A. The projection image as used herein means a pseudo two-dimensional image generated from the tomographic image. On the other hand, in the case of the inspection data D (1340) indicating the inspection data when the cross scan is performed, an arrow line 1343 indicating a cross line of the actual scan and the scan direction for acquiring the tomographic image is overlapped and displayed on the SLO thumbnail image 1340. However, this scan is not a scan of an area like the cross scan and cannot produce a sufficient projection image. Therefore, the projection image is not overlapped and displayed on the SLO thumbnail image.

The scanning pattern name 1317 expresses the above-mentioned scanning pattern by characters. Examples of the name are as follows. Because the inspection data A (1310) is acquired by the horizontal 3D scan with the center at a macular that is suitable for macular diagnosis, it is expressed as Macula 3D (papilla 3D). Because the inspection data B (1320) is acquired by the 3D scan with the center at a papilla, it is expressed as Disk 3D (papilla 3D). Because the inspection data C (1330) is acquired by the vertical 3D scan with the center at a macular that is suitable for glaucoma diagnosis, it is expressed as Glaucoma 3D. Because the inspection data D (1340) is acquired by the cross scan, it is expressed as Cross. Other than those, there are Multi Cross by multiple cross scans, and Anterior 3D (anterior ocular segment 3D) that is a 3D scan of the anterior ocular segment. In this way, by expressing the scanning pattern used for the photography with a name extracted from the characteristic, the operator can clearly know the scanning pattern of the past photography.

The QI value 1318 is an index indicating image quality of the tomographic image, namely an image quality index, which is a value of 0 to 10 calculated by an SNR method, for example. In this embodiment, the QI value is expressed by an indicator constituted of to squares and a value. The indicator is colored differently for ranges. For instance, the range of 1 to 2 is colored in red, the range of 3 to 6 is colored in orange, and the range of 7 to 10 is colored in green. Thus, it is possible to grasp the quality of images of the selected patient photographed in the past in an intuitive manner. Here, if a fixation state of the subject is poor, the image duality is generally deteriorated. Therefore, by looking through the QI value, it is possible to determine before photography whether or not the subject has a good fixation state, that is, whether or not the subject is easily photographed. In addition, this determination can be made also in the improper image display 1339. If There has been many improper images for the patient, because the display can be seen on the past examination list 1300, seeing the improper image information on the display can be an index of difficulty of photographing the patient.

With the structure described above, it is possible to provide the operator with an easy viewing examination list by which desired past inspection data can be efficiently retrieved and the difficulty of photographing the patient can be determined.

(Structure of Capture Screen)

With reference to FIG. 4A, a capture screen according to this embodiment is described. The capture screen is a screen for various settings and adjustments for acquiring a desired image of the eye to be inspected, and is a screen displayed on the monitor 928 before photography. An anterior ocular segment observation screen 2101 is obtained by the anterior ocular segment observation CCD 171. A two-dimensional image display screen 2201 of the eye to be inspected is obtained by the photodiode 173. A tomographic image display screen 2301 is a screen for checking the acquired tomographic image. A button 2001 is used for switching between the left and right of the eye to be inspected. By pressing an L or R button, the image acquiring portion 900 is moved to an initial position for she left or right eye.

An examination set selection screen 2010 displays a selected examination set. The examination set as used herein means a scanning pattern group in which at least one scanning pattern is stored together with an order of the scanning pattern. Examples of the examination set include a scanning pattern group suitable for maculopathy, a scanning pattern group suitable for glaucoma, and a scanning pattern group suitable for papilla analysis or anterior ocular segment analysis. In addition, there is also an examination set called "follow-up" described later, which has the same scanning pattern group as that photographed in the past. When the examination set is to be changed, the operator clicks a position 2011 so as to display a pulldown menu (not shown) and selects a desired examination set. In addition, a scanning pattern display screen 2012 displays an outline of the scanning pattern performed in the currently selected examination set, for example, the 3D scan, the cross scan, and the like sequentially.

A patient information display portion 2400 displays various information of the patient that is currently examined, namely a patient ID, a patient name, an age, and a sex, for example.

When an arbitrary point on the anterior ocular segment observation screen 2101 is clicked by the mouse, the acquiring portion 900 is moved so that the point becomes the screen center. Thus, alignment between the acquiring portion and the eye to be inspected is performed.

When a start button 2004 is pressed, acquiring of the tomographic image and the two-dimensional image is started, and acquired images of the eye to be inspected are displayed in real time in the two-dimensional image display screen 2201 and the tomographic image display screen 2301. In this case, a frame 2202 displayed in the two-dimensional image display screen 2201 indicates a range of acquiring the tomographic image in the photography. In addition, a horizontal arrow line 2203 at the center portion in the vertical direction indicates a position and a scanning direction on the eye to be inspected whose tomographic image is acquired and displayed on the tomographic image display screen 2301.

A slider disposed at a vicinity of each image is used for adjustment. A slider 2103 is used for adjusting a position of the acquiring portion in the Z direction with respect to the eye to be inspected, a slider 2203 is used for focus adjustment, and a slider 2303 is used for adjusting a position of a coherence gate.

The focus adjustment is an adjustment for focusing on a fundus by moving the lenses 135-3 and 135-5 in the illustrated direction. The coherence gate adjustment is an adjustment of moving the reference mirror 132-4 in the illustrated direction so that the tomographic image is observed at a desired position on the tomographic image display screen. By these adjustment operations, the operator creates a state where the optimal photography can be performed. A photography button 2003 is pressed after various adjustment operations are finished so that desired photography is performed.

(Structure of Tomographic Image Confirmation Screen)

Figure 4B:
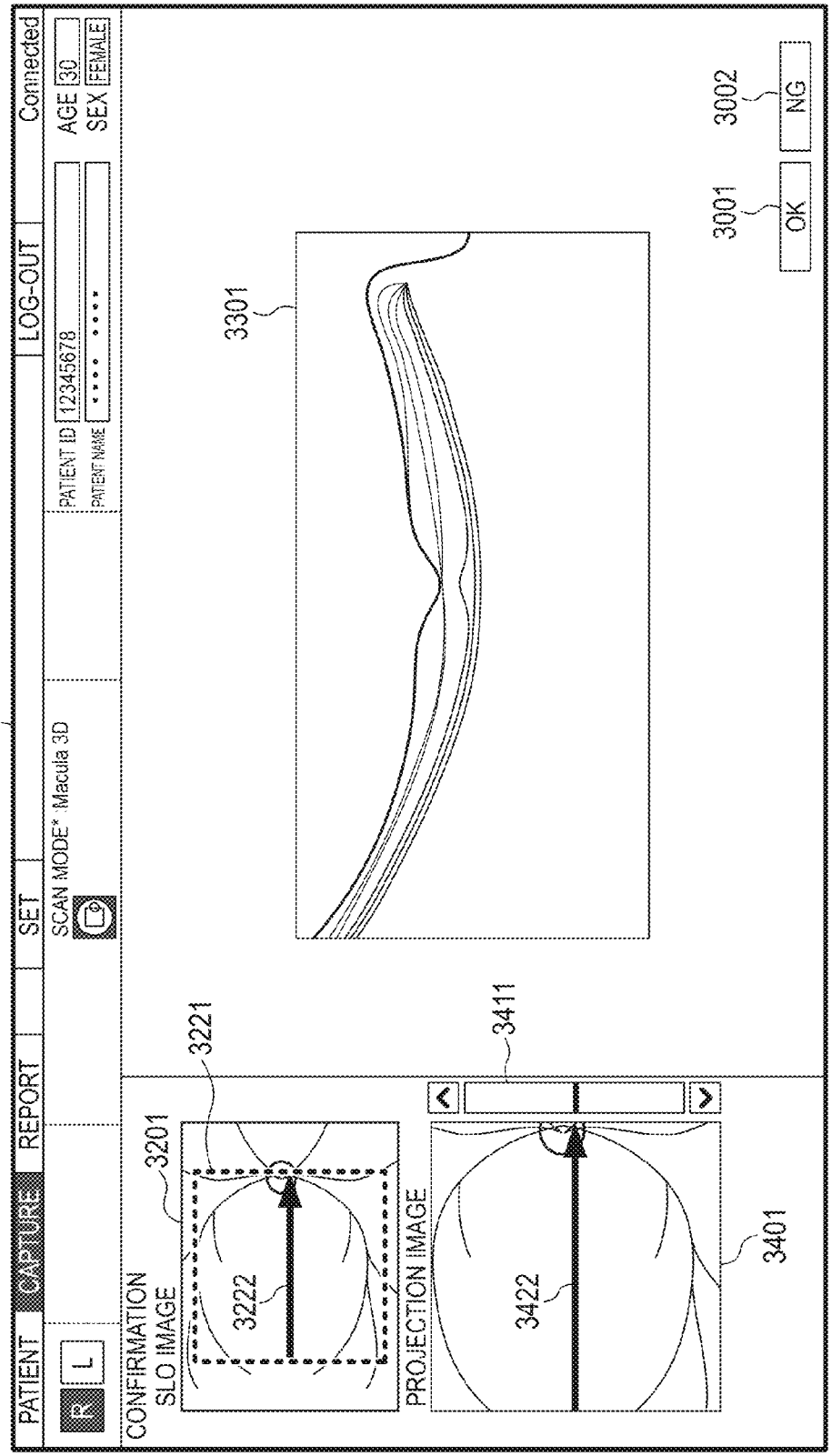
FIG. 4B is an example of an explanatory diagram of a confirmation screen for displaying a still image after photography on the same monitor.

Next, with reference to FIG. 4B, a confirmation screen 3000 according to this embodiment is described. The confirmation screen is a screen displayed on the monitor 928 after photography, on which the operator confirms whether or not the photographed tomographic image is an improper image. In addition, a lesion or the like is roughly checked so as to determine a section to be noted in the next photography.

A two-dimensional image display screen 3201 of the eye to be inspected is acquired by the photodiode 173 for acquiring the two-dimensional image. A tomographic image display screen 3301 is used for checking the acquired tomographic image. A projection image display screen 3401 displays a projection image that is an image of the eye to be inspected reconstructed or restructured from the acquired tomographic image. In addition, a slider 3411 is used for specifying a sectional position of the tomographic image displayed on the tomographic image display screen. Further, an NG button 3002 is clicked by the mouse or the like when the operator determines that the acquired tomographic image is an improper image, and an OK button 3001 is clicked by the mouse or the like when the operator determines that the acquired tomographic image is not an improper image but a good image.

In the two-dimensional image display screen 3201, there are displayed a tomographic image acquiring area 3221 and an arrow 3222 indicating an acquiring position and a scanning direction of the tomographic image illustrated in the tomographic image display screen 3301, namely a scanning locus and its outline as a schematic diagram. Similarly, also in the projection screen 3401, there is displayed an arrow 3422 indicating an acquiring position and a scanning direction of the tomographic image illustrated in the tomographic image display screen 3301.

In an initial state of this screen, a tomographic image at the center position in the tomographic image acquiring area 3221 is displayed on the tomographic image display screen 3301. In order to check the tomographic image in more detail, the operator operates the slider 3411. By this operation, the tomographic image displayed on the tomographic image display screen 3301 moves in the tomographic image acquiring area. Thus, the operator can check every tomographic image. Thus, the operator can check accurately whether or not the tomographic image is an improper image. In addition, the operator can roughly check a lesion or the like.

(Structure of Report Screen)

Figure 5A:
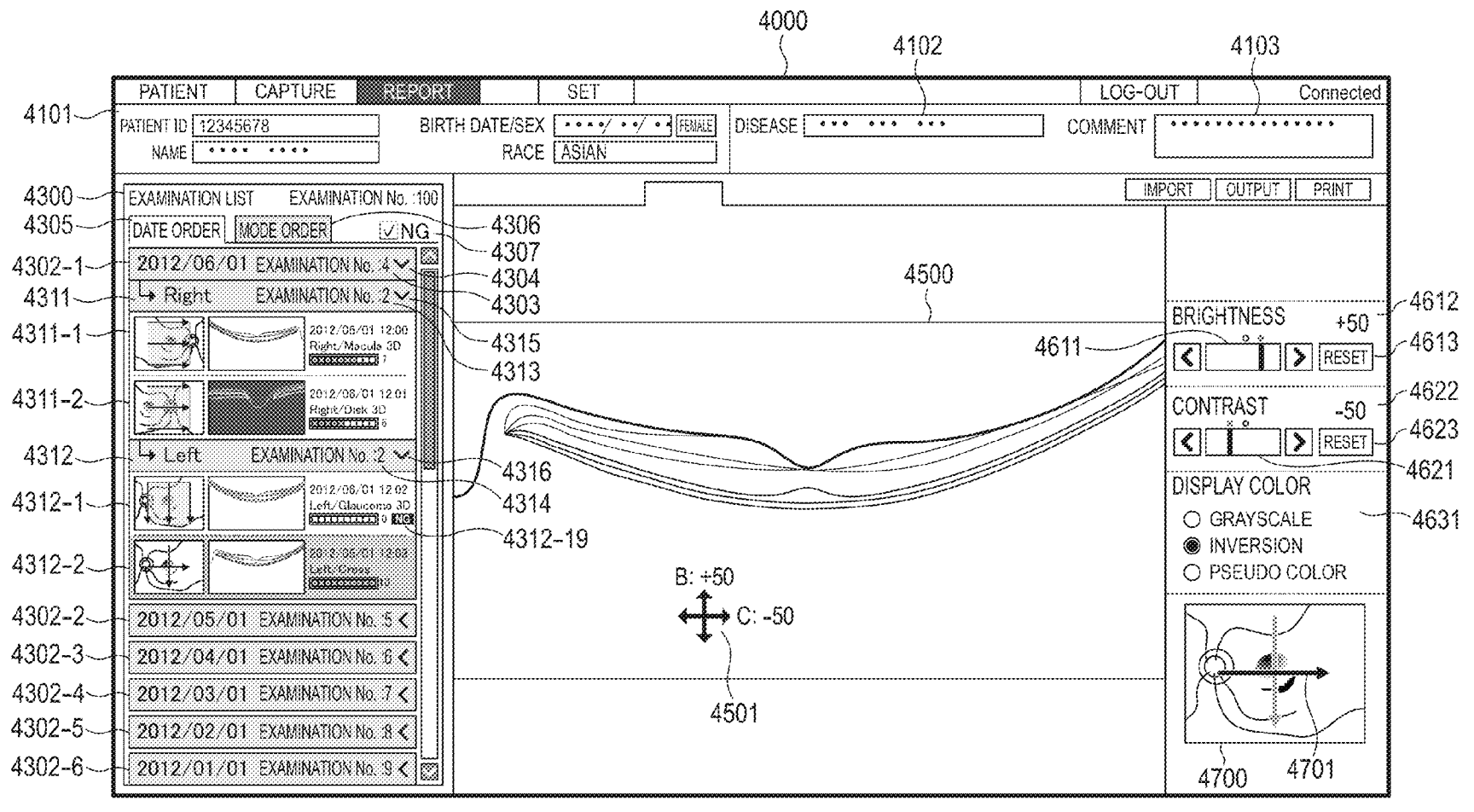

With reference to FIG. 5A, a report screen 4000 according to this embodiment is described. The report screen is a screen displayed on the monitor 928 and is a screen for checking and making diagnosis of the acquired image of the eye to be inspected in more detail than the confirmation screen.

A patient basic information display portion 4101 displays a patient ID, a patient name, a date of birth, a sex, and a race of the patient displayed on this screen. A disease name input portion 4102 is used by the operator to input a name of disease after making detailed analysis and diagnosis on this screen. A comment input portion 4103 is a screen in which the operator can freely input a comment. Here, in the report screen 4000, the patient basic information input in the patient basic information display portion 4101 cannot be edited, but the disease name input portion 4102 and the comment input portion 4103 can be edited.

An examination list display portion 4300 displays the past examination list of the patient selected in this screen. Description of the same part as the examination list 1300 in the patient screen 1000 is omitted. An NG check button 4307 is used for switching display/non-display of NG data. If this button is not checked, data determined to be NG on the confirmation screen 3000, that is, data with an NG flag as in 4312-19 is not displayed. On the other hand, if the button is checked, the data is displayed. A date order tab 4305 and a mode order tab 4306 are used for switching between a date priority and a mode priority of arrangement order of the inspection data. Here, a case where the date order tab 4305 is selected is described first.

If the date order tab is selected, pieces of individual inspection data are grouped by date of photography in the same manner as the examination list 1300 on the patient screen 1000. Tabs 4302-1 to 4302-6 are inspection data group date tabs in which the inspection data are grouped by date, and are displayed in a descending order so that the later date is displayed in the upper position. For instance, the date tab 4302-1 displays the date of photography, the number of inspection data 4303 of the date, and an expansion indicator 4304 indicating the expanded/collapsed state. In addition, the examination list 4300 on this screen is further divided into data groups of left and right eyes in the data group of each date. In a right eye tab 4311, pieces of inspection data of merely the right eye are grouped. In a left eye tab 4312, pieces of inspection data of merely the left eye are grouped. Each tab includes the numbers of inspection data 4313 and 4314 in the same manner as the date tab 4302-1. Further, expansion indicators 4315 and 4316 indicating the expanded/collapsed state are displayed side by side. Further, the respective left and right eye tabs display pieces of individual inspection data 4311-1, 4311-2, 4312-1, and 4312-2. A display content of each individual inspection data is the same as that of the examination list 1300 on the patient screen, and hence detailed description thereof is omitted.

Figure 5B:
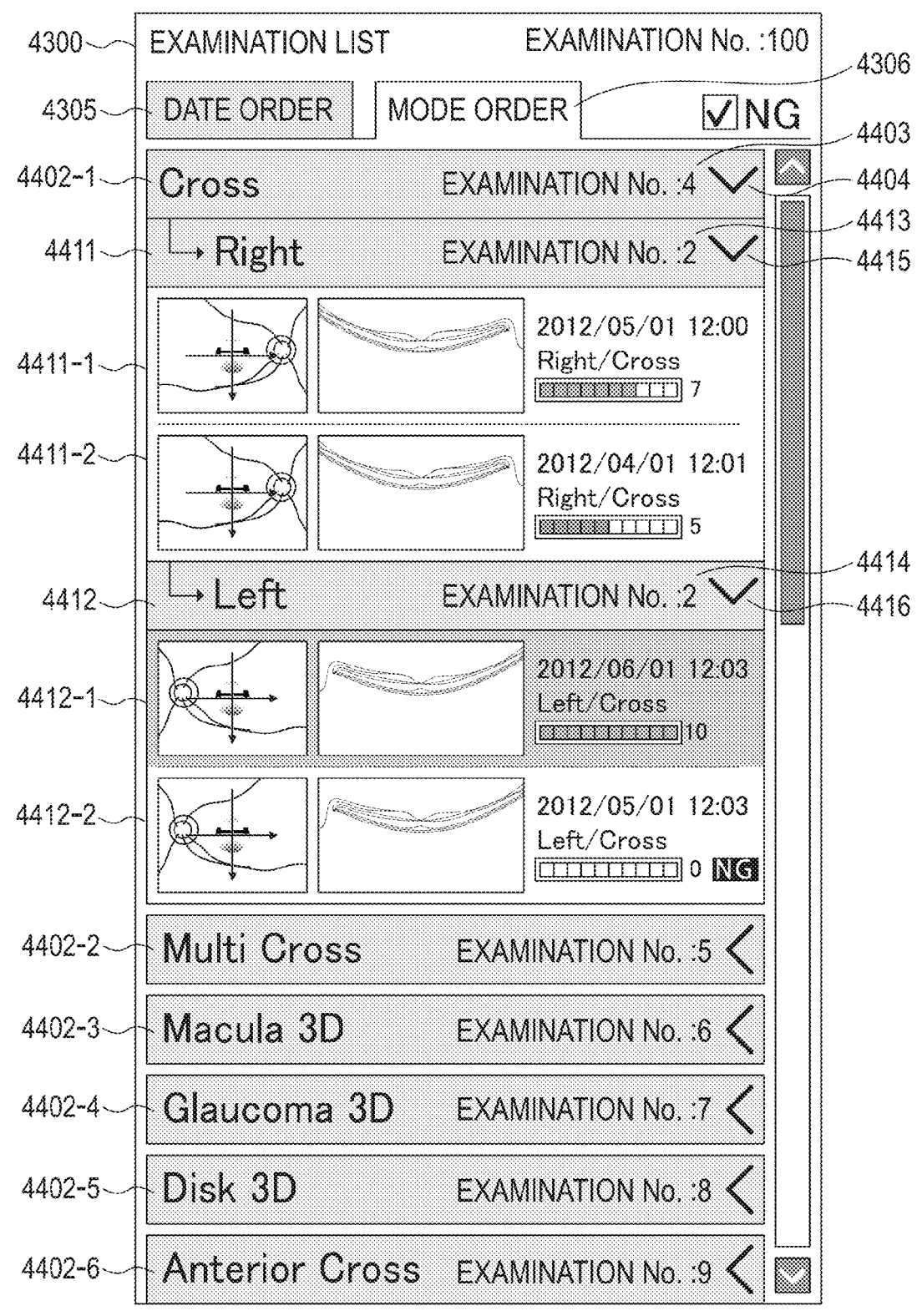

Next, a case where the mode order tab 4306 is selected is described with reference to FIG. 5B. If the mode order tab is selected, the pieces of individual inspection data are grouped based on the scanning pattern. Tabs 4402-1 to 4402-6 are inspection data group scanning pattern tabs in which the pieces of inspection data are grouped based on the scanning pattern. In this case, the scanning patterns for grouping include a cross pattern, a multi-cross pattern, a macular 3D pattern, a glaucoma 3D pattern, a papilla 3D pattern, an anterior ocular segment 3D pattern, and the like. For example, the scanning pattern tab 4402-1 displays a scanning pattern name, the number of inspection data 4403 of the date, and an expansion indicator 4404 indicating the expanded/collapsed state. In addition, similarly to the above-mentioned case where the date order tab is selected, the data group of each scanning pattern is further divided into data groups of the left and right eyes. In a right eye tab 4411, pieces of inspection data of merely the right eye are grouped. In a left eye tab 4412, pieces of inspection data of merely the left eye are grouped. The tabs respectively display the numbers of inspection data 4413 and 4414, and expansion indicators 4115 and 1416 indicating the expanded/collapsed state side by side similarly to the date tab 4402-1. Further, the respective tabs display pieces of individual inspection data 4411-1, 4411-2, 4412-1, and 4412-2. Details of each inspection data is the same as the examination list 1300 on the patient screen 1000, and hence overlapping description is omitted.

The past examination list 1300 on the patient screen 1000 is different from the past examination list 4300 on the report screen 4000 in the above description, but the past examination list 1300 and the examination list 4300 may be the same. For instance, the past examination list 1300 on the patient screen may also be sorted in the date order or the photography mode order.

A tomographic image display screen 4500 displays a tomographic image at a position indicated on a two-dimensional image display screen 4700 described later in the photography data selected in the examination list 4300. The two-dimensional image display screen 4700 displays a two-dimensional image of the eye to be inspected, which is acquired substantially simultaneously with the tomographic image displayed in the tomographic image display screen 4500. Here, the displayed two-dimensional image is a projection image if the tomographic image is acquired by the 3D scan, or an SLO image if the tomographic image is acquired by the cross scan or the multi-cross scan. In this case, because the case of the cross scan is illustrated, the SLO image is displayed on the two-dimensional image display screen 4700. In addition, in the two-dimensional image display screen, the scanning pattern when the tomographic image is acquired is displayed, and a line indicating a cross section displayed on the tomographic image display screen 4500 is displayed in an emphasized manner. Here, a line 4701 in the horizontal direction is displayed in an emphasized manner.

Here, image parameters of the tomographic image displayed on the tomographic image display screen 4500 can be adjusted by the following method.

A slider 4611 is a brightness adjustment slider. For instance, a set value is added to each pixel brightness value. The value can be set in a range of −150 to +150. Thus, the image can be brightened or darkened. The tomographic image is displayed on the tomographic image display screen 4500 at a set value 4612.

A slider 4621 is a contrast adjustment slider. For instance, each pixel brightness value is multiplied by a set value. The value can be set in a range of −100 to +100. For instance, if the value is −100, each pixel value is multiplied by ½. If the value is +100, each pixel value is multiplied by 2. Thus, it is possible to obtain a clear image in which signal intensity is amplified. The tomographic image is displayed on the tomographic image display screen 4500 at a set value 4622.

Reset buttons 4613 and 4623 disposed beside the sliders are reset buttons. By pressing the reset button, each parameter can be reset to an initial value of zero.

When a cursor is dragged by the mouse or the like in the tomographic image display screen 4500, a contrast/brightness (C/B) pointer 4501 is displayed. When the pointer is dragged in the left and right direction in the state where the C/B pointer is displayed, a contrast of the tomographic image display screen can be adjusted. When the pointer is dragged in the up and down direction, a brightness can be adjusted. In order to reset the image to an initial state, the above-mentioned reset button 4613 or 4623 is pressed, or a reset button (not shown) (for example, in a pulldown menu that becomes available by right click of the mouse) in the tomographic image display screen 4500 is operated.

In a display color changing portion 4631, display color of the tomographic image displayed on the tomographic image display screen 4500 can be changed. If a gray scale is selected for brightness information as an image parameter change, signal intensities are used, that is, a part of the eye to be inspected having a large reflection intensity is displayed in white, and a part having a small reflection intensity is displayed in black. If the brightness information is inverted as the image parameter change, a part having a large reflection intensity is displayed in black while a part having a small reflection intensity is displayed in white in the inverted display on the contrary to the gray scale. If a pseudo color is selected as the image parameter change so as to convert brightness information into color information, display is performed in a manner that different colors are assigned to different reflection intensity of light. For example, a part having a large reflection intensity is displayed in a warm color such as red while a part having a small reflection intensity is displayed in a cold color such as blue.

With the structure and adjustment of the image parameter described above, the operator can obtain an optimal tomographic image for each lesion so that more detailed diagnosis can be performed.

In addition, the adjustment and change contrast, brightness, and display color performed on the tomographic image displayed on the tomographic image display screen 4500 are also reflected on the examination list 4300 of the report screen and on the tomographic thumbnail image of the examination list 1300 on the patient. screen. Thus, even on the examination list, characterized thumbnail images can be displayed, and hence efficiency in searching for a desired inspection data can be improved.

Note that, the present invention is not limited to this structure. For instance, it is possible to adopt a structure in which contrast and the like of an image such as the displayed tomographic image can be adjusted on the confirmation screen 3000 in the same manner as on the report screen 4000. Specifically, on the confirmation screen 3000, the brightness adjustment slider 4611, the brightness value 4612, the brightness reset button 4613, the contrast adjustment slider 4621, the contrast value 4622, the contrast reset button 4623, the display color changing portion 4631, and the C/B adjustment pointer 4501 may be displayed. In this case, adjustment performed on the image on the confirmation screen 3000 is reflected on the thumbnail image of the past examination list 4300 displayed on the report screen 4000. In addition, it is possible to display the two-dimensional image display screen 4700 on the confirmation screen 3000.

As to the display of the patient screen 1000, the capture screen 2000, the confirmation screen 3000, and the report screen 4000 described above, a module region of the personal computer 925 functioning as a display control unit generates and designates the display content. The monitor 928 as a display unit displays images in accordance with an instruction from the display control unit. In addition, the monitor 928 also functions as a display input unit for receiving an external input via an image displayed on the display unit, such as selection of the L or R button.

(Operation Flow)

An operation flow in this embodiment is described with reference to FIGS. 6A and 6B. First, when the examination is started in Step S1, the personal computer 925 executes the examination program and displays the patient screen 1000 on the monitor 928 in Step S2. In Step S3, the operator inputs patient information to the patient information input portion 1100. Next, in Step S4, whether or not there is a patient corresponding to the information input in Step S3 is retrieved from the patient information storage portion. In Step S5, it is determined whether or not there is a relevant patient. If the relevant patient is stored in the patient information storage portion, the process proceeds to Step S6 in which the relevant patient is displayed. Here, by displaying the relevant patient by the incremental search method described above, a retrieve result can be checked quickly. Next, the process proceeds to Step S7. If multiple relevant patients are displayed, the operator selects one desired patient among them. Alternatively, if there is only one relevant patient, the patient is automatically selected. After the one patient is selected, the process proceeds to Step S8, and the past examination list 1300 of the selected patient is displayed. Next, the operator selects one inspection data from the past examination list in Step S9. In this case, the operator searches for the inspection data while viewing the thumbnail images, and hence can roughly grasp diseases, a position of a lesion, a fixation state, and the like of the patient. In Step S10, a transit to the capture screen is instructed in a state where the one inspection data is selected. For instance, the tab button 1002 for transiting to the capture screen is pressed. Then, in Step S11, the capture screen 2000 is displayed. If the patient information is not registered in the patient information storage portion in Step S5, that is, if the patient is a new patient, the process proceeds directly to this Step S10 without the display of the past examination and the selection, and it is determined whether or not to transit to the capture screen.

In Step S11, the capture screen 2000 is displayed on the monitor 928. Here, the operator first selects the examination set on the examination set selection screen 2010 (Step S12). In this case, if the follow-up examination selected, based on the inspection data selected in Step S9, the scanning pattern group, the scanning position, the focus position, and the like when the data is acquired are read from the patient information storage portion for performing automatic reproduction. Thus, the tomographic image of the eye to be inspected can be newly acquired in the same condition as the past data to be compared. For instance, if the inspection data 1310 of the past examination list 1300 is selected in Step S9, the examination set having the number of examinations of four displayed in the tab 1302-1 is automatically reproduced as the follow-up examination. After the examination set is selected in Step S12, the operator acquires an image in Step S13. After that, the above-mentioned confirmation screen 3000 is displayed in Step S14, and based on the image, the operator determines in Step S15 whether or not the image photographed in Step S13 is an improper image. If the image is not an improper image, the process proceeds to Step S16 in which it is determined whether or not the photography of the scanning pattern group in the examination set selected in Step S12 is completed. On the other hand, if it is determined that the image is an improper image, the image is stored in the patient information storage portion together with NG information, and then the process returns to Step S11 to acquire the image again.

If it is determined in Step S16 that the photography of the scanning pattern group in a predetermined examination set is completed, the operator selects in Step S17 whether or not to transit to the report screen. If it is selected to transit to the report screen, the process proceeds to Step S18 in which the report screen 4000 is displayed. On the other hand, if it is selected not to transit to the report screen, the process proceeds to Step S23. When the report screen is displayed in Step S18, the past examination list 4300 is displayed in Step S19, and the operator selects desired inspection data from the past examination list. Here, the past examination list 4300 includes thumbnails of the images that are photographed in Step S13 and are acquired from the image acquiring portion 900 by the personal computer 925. In other words, a module region of the personal computer 925 functioning as an acquiring unit acquires an image of the object to be inspected, and further a module region of the personal computer 925 functioning as an image generation unit generates the thumbnail image. A tomographic image of the selected inspection data is displayed on the monitor 928 in Step S20 as illustrated in the report screen 4000 described above. By observing this screen, the operator performs detailed diagnosis and investigation.

Here, in Step S21, it is possible to change the image parameters (brightness, contrast, and display color) so that the feature of the tomographic image can be grasped more easily. If the image parameter is changed, the information is stored in the patient information storage portion in Step S22. Next, in Step S23, based on the information in the patient information storage portion, the thumbnail image of the past examination list 1300 on the patient screen and a thumbnail image of the past examination list 4300 on the report screen are changed. Note that, the image parameter change in the thumbnail image may be performed only on an image displayed in highlight or on every image. For instance, in order to compare images, it is conceivable to adjust brightness values to be the same value for comparing the highlight image with the acquired image. However, in order to compare inverted images, it is conceivable to invert all the thumbnail images for roughly comparing with the acquired image. In addition, the image parameter change may be performed only on the latest images of a predetermined number designated in advance or images having a predetermined condition. Thus, the tomographic thumbnail image displayed in the past examination list can be a thumbnail image whose feature can be easily grasped. Thus, the operator can retrieve desired inspection data quickly and easily. Step S24 is a step to be performed after Step S23 or if the image parameter is not changed in Step S21. In Step S24, it is determined whether or not to perform additional photography. If the additional photography is performed, the process returns to Step S11 in which the capture screen 2000 is displayed. In contrast, if the additional photography not performed, the process proceeds to Step S25. In Step S25, if the operator presses the transit button 1001 to a patient button for changing the patient, the process returns to Step S2, and the flow described above is repeated. In contrast, if the patient is not changed, the operator presses the log out button 1005 so that the examination program is ended. The process proceeds to Step S26, and the examination is ended.

As described above, the display control unit controls the monitor 928 to list patients whose information is stored in the patient information storage unit as the patient information and list thumbnail images of the patient information selected by the display input unit. In addition, the monitor 923 as the display input unit accepts an input for selecting one patient from the patient list and an input for changing at least one image parameter of the displayed image. The personal computer 925 functioning as the display control unit further includes a module region functioning as an image parameter changing unit. As described above, in accordance with the input image parameter, the image parameter of the thumbnail image is changed so that the image is reconstructed and is displayed on the monitor 928. The structure described above constructs an image processing unit for reflecting the image processing performed on the image acquired by the image acquiring unit or the acquiring unit in the present invention also on the thumbnail image.

Further, the display control unit may control the display unit to display, together with the thumbnail image, at least one of the photographed date and time, the left/right information of the photographed eye, and the measuring light scanning pattern. Alternatively, the display control unit may control the display unit to display, together with the thumbnail image, the image quality index described above. In addition, the improper image information determined by the operator may be stored for each acquired tomographic image and may be displayed together with the thumbnail image. Further, the reconstructed two-dimensional image may be overlapped and displayed on the thumbnail image of the two-dimensional image, or a schematic diagram of the scanning locus when the eye to be inspected is scanned may be overlapped on the thumbnail image of the two-dimensional image. In addition, as described above, it is preferred to use a tomographic image at a center scanning line position as a thumbnail image of the tomographic image.

By performing the photography in accordance with the above-mentioned flow, the tomographic thumbnail image in the examination list can be presented to the operator as an image whose feature can be easily grasped. Therefore, the operator can retrieve desired past inspection data easily and quickly, and hence it is possible to improve examination efficiency and diagnosis efficiency.

In other words, according to the present invention, by acquiring the two-dimensional image of the eye to be inspected by confocal laser scanning using near-infrared light called SLO, it is possible to acquire a high contrast two-dimensional image While reducing miosis. Therefore, the two-dimensional image of the eye to be inspected that is acquired substantially simultaneously with the tomographic image can be presented to the operator, and hence the operator can easily and quickly determine which section of the eye to be inspected is focused on and photographed to acquire the tomographic image.

In addition, when similar past photographed images are displayed, it is possible to present information for searching for desired photography data.

In addition, it is possible to present to the operator how good image quality can be obtained by photographing the patient, that is, how good or poor a fixation state of the subject is, easily and gradually, prior to the photography.

In addition, it is possible to present to the operator whether or not the patient is apt to generate an improper image, that is, whether or not the patient is easy to photograph, prior to the photography.

In addition, because the two-dimensional image reconstructed from the tomographic image is presented to the operator, the operator can estimate deep vessels and lesions of the eye to be inspected from the two-dimensional image to a certain extent.

In addition, because the schematic diagram of the scanning pattern for acquiring the tomographic image is overlapped on the two-dimensional image of the eye to be inspected, it is possible to present to the operator the scanning pattern that is used for the photography in a more intuitive manner.

In addition, by utilizing a fact that the photography is performed usually with respect to the noted section as the center, the tomographic thumbnail image whose feature can be easily grasped can be provided to the operator with a simple structure.

In addition, when a desired patient is searched for from the patient data group, it is not necessary to input all characters of the word to be searched for, and an input error can be dealt with quickly. Therefore, the patient search efficiency can be improved.

Further, because the past inspection data can be sorted in an order desired by the operator, it is possible to present the past inspection data in a manner corresponding to a priority order for the operator to select the past examination. Therefore, efficiency of searching for past inspection data by the operator can be improved.

(Other Embodiment)

Further, the present invention can also be realized by performing the following processing. That is, the processing involves supplying software (program) for realizing the functions of the above-mentioned embodiment to a system or an apparatus via a network or various storage media and causing a computer (or a CPU, an MPU, or the like) of the system or the apparatus to read and execute the program.

The present invention is not limited to the above-mentioned embodiment and can be variously modified or changed within a scope without departing from the spirit of the present invention. For example, in the above-mentioned embodiment, the case where an object to be inspected is an eye has been described, but the present invention can also be applied to objects to be measured such as a skin and an organ except an eye. In this case, the present invention has an aspect as medical equipment such as an endoscope except an ophthalmologic apparatus. Therefore, it is desired that the present invention be understood as an optical tomographic imaging apparatus exemplified by an ophthalmologic apparatus, and the eye to be inspected be understood as one aspect of the object to be inspected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-189802, filed Aug. 30, 2012, which is hereby incorporated by reference herein in its entirety.

What is claimed is:

1. An optical tomographic imaging system, comprising:
    a tomographic image acquiring unit for acquiring a tomographic image by scanning an object to be inspected with measuring light;
    a two-dimensional image acquiring unit for acquiring a two-dimensional image of the object to be inspected; and
    a display control unit for controlling a display unit to display both a thumbnail image of the tomographic image and a thumbnail image of the two-dimensional image,
    wherein the display control unit causes the display unit to overlap a schematic diagram of a scanning locus for scanning the eye to be inspected by the tomographic image acquiring unit on the thumbnail image of the two-dimensional image, and
    wherein the display control unit is configured to control the display unit to display the tomographic image, and reflect on the thumbnail image of the tomographic image an image process performed on the tomographic image displayed on the display unit.

2. An optical tomographic imaging system according to claim 1, wherein the two-dimensional image acquiring unit comprises a scanning type two-dimensional image acquiring unit, which is configured to scan the object to be inspected with measuring light for two-dimensional images so as to acquire the two-dimensional image.

3. An optical tomographic imaging system according to claim 1, wherein the image process comprises a change of at least one of brightness and contrast.

4. An optical tomographic imaging system according to claim 1, wherein the image process comprises one of inversion of brightness information and conversion from brightness information to color information.

5. An optical tomographic imaging system according to claim 1, wherein the object to be inspected comprises an eye to be inspected, and the display control unit is configured to control the display unit to display at least one of photography date and time of the tomographic image, left/right information of the eye to be inspected, and a scanning pattern of the measuring light, together with the thumbnail image of the tomographic image and the thumbnail image of the two-dimensional image.

6. An optical tomographic imaging system according to claim 1, wherein the display control unit is configured to control the display unit to display an image quality index together with the thumbnail image of the tomographic image and the thumbnail image of the two-dimensional image.

7. An optical tomographic imaging system according to claim 1, wherein the display control unit is configured to control the display unit to display information designating an improper image, together with the thumbnail image of the tomographic image and the thumbnail image of the two-dimensional image, the improper image being an image determined as improper by an operator.

8. An optical tomographic imaging system according to claim 1, wherein the display control unit is configured to overlap a two-dimensional image constructed from the tomographic image acquired by the tomographic image acquiring unit on a thumbnail image of the two-dimensional image.

9. An optical tomographic imaging system according to claim 1, wherein the display control unit is configured to use a tomographic image at a center scanning line position among a plurality of scanning lines corresponding to a plurality of tomographic images, respectively, as a thumbnail image of the tomographic image.

10. An optical tomographic imaging system according to claim 1, wherein the display control unit is configured to control the display unit to display a plurality of sets of both the thumbnail image of the tomographic image and the thumbnail image of the two-dimensional image, and enable sorting of the plurality of sets by assigning a first priority to one of a photography date and time order, a scanning pattern order, and a left/right eye order, and assigning a second priority to a remaining one of the orders.

11. An optical tomographic image display method for displaying an image acquired by an optical tomographic imaging system,
    the optical tomographic imaging system comprising:
        a tomographic image acquiring unit for acquiring a tomographic image by scanning an object to be inspected with measuring light; and
        a two-dimensional image acquiring unit for acquiring a two-dimensional image of the object to be inspected, and
    the display method comprising:
        controlling a display unit to display both a thumbnail image of the tomographic image and a thumbnail image of the two-dimensional image, to overlap a schematic diagram of a scanning locus for scanning the eye to be inspected by the tomographic image acquiring unit on the thumbnail image of the two-dimensional image, to display the tomographic image, and to reflect on the thumbnail image of the tomographic image an image process performed on the tomographic image displayed on the display unit.

12. A non-transitory tangible medium having stored thereon a program for causing a computer to execute the steps of the optical tomographic image display method according to claim 11.

13. An optical tomographic imaging system according to claim 1, wherein the object to be inspected is a fundus of an eye.

14. An optical tomographic imaging system according to claim 1, further comprising a selection unit configured to select first patient information among a plurality of patient information displayed on the display unit,
wherein the display control unit controls the display unit to display both the thumbnail image of the tomographic image and the thumbnail image of the two-dimensional image which are associated with the first patient information selected by the selection unit.

15. An optical tomographic imaging system according to claim 1, wherein a size of the thumbnail image of the tomographic image is smaller than a size of the tomographic image.

* * * * *